United States Patent
Murakami et al.

(10) Patent No.: US 8,747,635 B2
(45) Date of Patent: Jun. 10, 2014

(54) GAS SENSOR

(75) Inventors: Mika Murakami, Aichi (JP); Naoya Saito, Aichi (JP); Tomoya Seimori, Aichi (JP)

(73) Assignee: NGK Insulators, Ltd., Nagoya-shi, Aichi ( * ) Notice: Subject to any disclaimer, the term of this patent is extended or adjusted under 35 U.S.C. 154(b) by 147 days.

(21) Appl. No.: 13/413,933

(22) Filed: Mar. 7, 2012

(65) Prior Publication Data

US 2012/0247957 A1    Oct. 4, 2012

(30) Foreign Application Priority Data

Mar. 31, 2011    (JP) .................. 2011-078373

(51) Int. Cl.
*G01N 27/409*    (2006.01)
*G01N 27/26*     (2006.01)
*G01N 27/41*     (2006.01)

(52) U.S. Cl.
USPC .......... 204/429; 204/424; 204/428; 204/427; 204/426; 73/23.31; 73/23.32

(58) Field of Classification Search
USPC .................. 204/421–429; 73/23.31, 23.32
See application file for complete search history.

(56) References Cited

U.S. PATENT DOCUMENTS

| | | |
|---|---|---|
| 2005/0077177 A1 | 4/2005 | Sakayanagi |
| 2005/0230250 A1* | 10/2005 | Imamura et al. ............. 204/426 |
| 2011/0186431 A1* | 8/2011 | Horisaka et al. ............. 204/424 |

FOREIGN PATENT DOCUMENTS

| | | |
|---|---|---|
| DE | 101 54 869 C1 | 5/2003 |
| EP | 2 082 870 A2 | 7/2009 |
| EP | 2 105 729 A1 | 9/2009 |
| JP | 2003-149199 A | 5/2003 |
| JP | 2006-284223 A | 10/2006 |

OTHER PUBLICATIONS

European Search Report of the corresponding European Appication No. 12158098.8, dated Jul. 18, 2012.

\* cited by examiner

*Primary Examiner* — Jennifer Dieterle

(74) *Attorney, Agent, or Firm* — Global IP Counselors, LLP

(57) ABSTRACT

A gas sensor is provided with a multilayer body of solid electrolyte layers, a measurement electrode, a reference electrode, a reference gas introduction layer, a detection unit and a heater. The reference electrode and the measurement electrode are formed directly on the same first solid electrolyte layer. Thus, heat from the heater is transferred from a third substrate layer to the first solid electrolyte layer, and also to the reference electrode and the measurement electrode through the same first solid electrolyte layer. The reference electrode is covered with a reference gas introduction layer, formed of a porous body. The transference of heat from the heater to the reference electrode through the reference gas introduction layer is smaller than the transference of heat from the heater to the reference electrode through the first solid electrolyte layer on which the reference electrode is formed directly.

6 Claims, 3 Drawing Sheets

GAS SENSOR

BACKGROUND OF THE INVENTION

1. Field of the Invention

The present invention relates to gas sensors.

2. Description of the Related Art

To date, a gas sensor that detects the concentration of a specified gas such as NOx included in an object gas such as an exhaust gas from an automobile has been known. For example, Patent Literature 1 discloses a gas sensor including a long plate-shaped sensor element formed of a plurality of gas-tight oxygen ion conductive solid electrolyte layers stacked one on top of one another. In this sensor element, a measurement electrode and a reference electrode are formed on separate solid electrolyte layers. An object gas is introduced on the measurement electrode side and a reference gas is introduced on the reference electrode side, and the concentration of a specified gas in the object gas is detected in accordance with an electromotive force generated between the reference electrode and the measurement electrode.

FIG. 6 is a schematic sectional view generally illustrating the structure of an example of such a related-art gas sensor 300. As illustrated in FIG. 6, the gas sensor 300 includes a sensor element 307. The sensor element 307 has a structure in which oxygen ion conductive dense solid electrolyte layers 301 to 306 are stacked one on top of one another. In the sensor element 307, an object gas flow path 310 is formed between a lower surface of the solid electrolyte layer 306 and an upper surface of the solid electrolyte layer 304. The object gas is introduced through the object gas flow path 310. A reference gas introduction space 343 is formed between an upper surface of the solid electrolyte layer 303 and a lower surface of the solid electrolyte layer 305. The reference gas is introduced through the reference gas introduction space 343. The concentration of a specified gas in the object gas is detected with reference to the reference gas. A measurement electrode 344, which is a porous cermet electrode, is formed directly on the upper surface of the solid electrolyte layer 304 that faces the object gas flow path 310. A reference electrode 342 is formed directly on the upper surface of the solid electrolyte layer 303 that faces the reference gas introduction space 343. The reference electrode 342 is covered with a reference gas introduction layer 348 formed of a porous body. The reference gas is introduced from the reference gas introduction space 343 through the reference gas introduction layer 348. The concentration of the specified gas in the object gas introduced into the object gas flow path 310 is detected in accordance with an electromotive force Va generated between the measurement electrode 344 and the reference electrode 342. A heater 372 is formed between the solid electrolyte layer 302 and the solid electrolyte layer 303. The heater 372 is insulated from the solid electrolyte layers 302 and 303 using a heater insulation layer 374. The heater 372 heats and increases the temperatures of the solid electrolyte layers 303 and 304 to cause the solid electrolyte layers 303 and 304 to be activated, thereby increasing the electrical conductivity of oxygen ions between the measurement electrode 344 and the reference electrode 342. A pressure releasing hole 375 is formed in the solid electrolyte layer 303 in order to suppress an increase in an internal pressure occurring as the temperature in the heater insulation layer 374 increases.

Patent Literature 1: JP 2006-284223 A

SUMMARY OF THE INVENTION

The above-described related-art gas sensor has a problem in that variation of the electromotive force is increased due to the temperature difference between the measurement electrode and the reference electrode. For example, in the gas sensor 300 illustrated in FIG. 6, heat from the heater 372 is transferred to the measurement electrode 344 through the solid electrolyte layers 303 and 304. With regard to the reference electrode 342, since the upper side of the reference electrode 342 in FIG. 6 is covered with the reference gas introduction layer 348 formed of the porous body, the heat from the heater 372 is not easily transferred through the solid electrolyte layer 304 and is easily transferred through the dense solid electrolyte layer 303 with which the reference electrode 342 is in direct contact. When the temperature difference between the reference electrode 342 and the measurement electrode 344 is increased due to the above-described difference in heat transference, variation in the electromotive force is increased. When the electromotive force varies, values of the electromotive force are different from one another even when, for example, the concentration of a specified gas in the object gas flow path 310 is the same. This may degrade accuracy in detecting the concentration of the specified gas.

The present invention is proposed in view of the above-described problem. A main object of the present invention is to decrease variation in electromotive force generated between the reference electrode and the measurement electrode in the gas sensor.

According to the present invention, the following means are taken in order to achieve the above-described object.

A gas sensor according to the present invention includes: a multilayer body formed of a plurality of oxygen ion conductive dense solid electrolyte layers stacked one on top of one another. The multilayer body has therein an object gas flow path through which an object gas is introduced from one end of the multilayer body, and a reference gas introduction space through which a reference gas is introduced from the other end of the multilayer body. A concentration of a specified gas in the object gas is detected with reference to the reference gas; a measurement electrode formed directly on one of the solid electrolyte layers facing the object gas flow path; a reference electrode formed directly on a surface of the one solid electrolyte layer on which the measurement electrode is formed, the surface being a surface on a side opposite a side on which the measurement electrode is formed; a reference gas introduction layer that covers the reference electrode, is formed of a porous body and formed so as to be exposed to the reference gas introduction space only on the other end side of the multilayer body at a position further away from the one end than the reference electrode is. The reference gas is introduced through the reference gas introduction layer from the reference gas introduction space to the reference electrode; a detection unit that detects the concentration of the specified gas in the object gas in accordance with a first electromotive force generated between the reference electrode and the measurement electrode; and a heater formed on the side of the reference electrode opposite a side on which the one solid electrolyte layer is disposed. The one solid electrolyte layer is a layer on which the reference electrode is formed directly thereon.

In this gas sensor, the reference electrode is formed directly on the surface of the dense solid electrolyte layer, on which the measurement electrode is formed, on the side opposite the side on which the measurement electrode is formed. That is, the reference electrode and the measurement electrode are formed directly on the same solid electrolyte layer. Thus, heat from the heater is transferred to the reference electrode and the measurement electrode through the same solid electrolyte layer. Since the reference electrode is covered with the reference gas introduction layer formed of a porous body, compared to transference of heat from the heater to the reference electrode through the dense solid electrolyte layer on which the reference electrode is formed directly thereon, transference of heat from the heater to the reference electrode through the reference gas introduction layer is decreased. Thus, compared to a gas sensor, for example, the gas sensor 300 illustrated in FIG. 6, in which a reference electrode and a measurement electrode are formed on the different solid electrolyte layers and not only the solid electrolyte layer but also a reference gas introduction layer are present between the reference electrode and the measurement electrode, occurrence of a situation that causes the temperature difference between the reference electrode and the measurement electrode due to heat from the heater is suppressed. This can decrease variation in the first electromotive force generated between the reference electrode and the measurement electrode.

The gas sensor according to the present invention may further include a main pump cell that applies a control voltage between an outer main pump electrode and an inner main pump electrode in accordance with a second electromotive force to pump oxygen into or out of the object gas flow path using the inner main pump electrode and the outer main pump electrode such that a concentration of oxygen in the object gas flow path reaches a specified main pump target concentration. In this case, the inner main pump electrode is formed on a solid electrolyte facing the object gas flow path, the outer main pump electrode is disposed on an outer surface of the multilayer body, the second electromotive force is generated between the inner main pump electrode and the reference electrode. The solid electrolyte on which the inner main pump electrode is formed directly may be the one solid electrolyte layer on which the measurement electrode is formed. Thus, occurrence of a situation that causes the temperature difference between the reference electrode and the inner main pump electrode is suppressed. This can decrease variation in the second electromotive force generated between both the electrodes.

The gas sensor may further include an auxiliary pump cell that applies another control voltage between an outer auxiliary pump electrode and an inner auxiliary pump electrode in accordance with a third electromotive force to pump oxygen into or out of the object gas flow path using the inner auxiliary pump electrode and the outer auxiliary pump electrode such that the concentration of oxygen in the object gas flow path reaches a specified auxiliary pump target concentration. In this case, the inner auxiliary pump electrode is formed on one of the solid electrolyte layers facing the object gas flow path, the outer auxiliary pump electrode is disposed on the outer surface of the multilayer body, the third electromotive force is generated between the inner auxiliary pump electrode and the reference electrode.

In the gas sensor including the main pump cell and the auxiliary pump cell formed as described above, the solid electrolyte layer on which the inner auxiliary pump electrode is formed directly may be the one solid electrolyte layer on which the measurement electrode is formed. Thus, occurrence of a situation that causes the temperature difference between the reference electrode and the inner auxiliary pump electrode is suppressed. This can decrease variation in the third electromotive force generated between both the electrodes.

The gas sensor including main pump cell and the auxiliary pump cell formed as described above may further include a plurality of leads each electrically connected to a corresponding one of the measurement electrode, the reference electrode, the inner main pump electrode, and the inner auxiliary pump electrode in a one-to-one relationship, and is formed so as to extend toward the other side of the multilayer body. In this case, the reference gas introduction space is a hole formed in another solid electrolyte layer of the plurality of solid electrolyte layers. The another solid electrolyte layer contacts the surface of the one solid electrolyte layer on the reference electrode side, and the reference electrode is formed directly on the one solid electrolyte layer. In this case, the plurality of leads are, when a direction perpendicular to a direction in which the solid electrolyte layers of the multilayer body are stacked is a lateral direction, laterally symmetrically arranged in a section. This section is perpendicular to a direction extending from the one end to the other end of the multilayer body on the other end side further away from the one end side than the measurement electrode, the reference electrode, the inner main pump electrode, and the inner auxiliary pump electrode are. Thus, the leads are laterally symmetrically arranged, compared to a case in which the leads are laterally asymmetrically arranged, warpage of the multilayer body in the lateral direction, which is caused by the difference in the thermal expansion coefficient between the leads and the solid electrolyte layers, is decreased.

In the gas sensor according to the present invention, the heater may be formed at a position away from the reference electrode with the other solid electrolyte layer interposed therebetween. In this case, the other solid electrolyte layer contacts the surface of the one solid electrolyte layer on the reference electrode side, and the one solid electrolyte layer is a layer on which the reference electrode is formed directly thereon. Thus, compared to a case in which two or more solid electrolyte layers are arranged between the reference electrode and the heater, the distance between the heater and the reference electrode and the distance between the heater and the measurement electrode are decreased, thereby suppressing occurrence of a situation that causes the temperature difference between the reference electrode and the measurement electrode. The gas sensor according to the present invention may include a heater insulation layer formed of a porous body, is formed between the heater and at least one of the solid electrolyte layers disposed adjacent to the heater, and insulates the heater from the at least one adjacent solid electrolyte layer. In this case, the reference gas introduction space is a hole formed in another solid electrolyte layer of the plurality of solid electrolyte layers. The another solid electrolyte layer contacts the surface of the one solid electrolyte layer on the reference electrode side, and the reference electrode is formed directly on the one solid electrolyte layer. In this case, part of the heater insulation layer is exposed to the reference gas introduction space. Thus, the reference gas introduction space also functions as a pressure releasing hole for the heater, thereby eliminating the need of forming a separate pressure releasing hole. That is, the internal pressure of the heater insulation layer formed of a porous body may increase because of expansion of a gas in the holes of the porous body due to heat from the heater. However, because of exposure of the heater insulation layer to the reference gas introduction space, the increase in the internal pressure can be suppressed by releasing the gas in the porous body to the reference gas introduction space.

DESCRIPTION OF THE PREFERRED EMBODIMENTS

Figure 1:
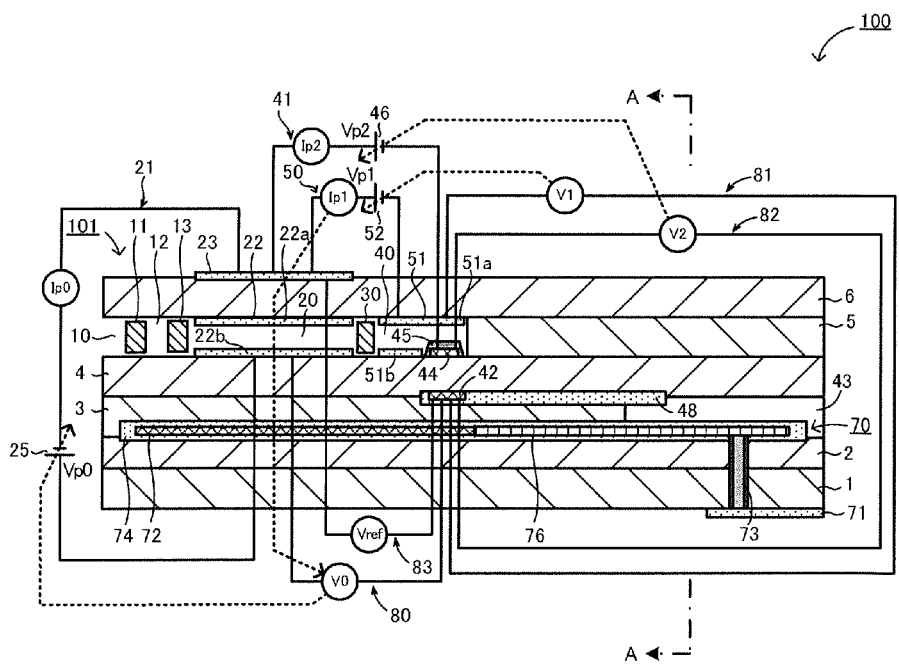
FIG. 1 is a schematic sectional view of a gas sensor 100.

Next, a general structure of a gas sensor 100, which is an example of an embodiment according to the present invention, will be described. FIG. 1 is a schematic sectional view generally illustrating an example of the structure of the gas sensor 100. The gas sensor 100 includes a sensor element 101 that detects the concentration of NOx in an object gas.

The sensor element 101 includes the following six layers, each of which is formed of an oxygen ion conductive solid electrolyte layer such as zirconia ($ZrO_2$), stacked one on top of one another in the following order from the lower side as seen in FIG. 1. That is, a first substrate layer 1, a second substrate layer 2, a third substrate layer 3, a first solid electrolyte layer 4, a spacer layer 5, and a second solid electrolyte layer 6. The solid electrolyte that forms these six layers is dense and gas-tight. Such a sensor element 101 is produced, for example, as follows. That is, a ceramic green sheet corresponding to each layer undergoes processes including specified processes and printing processes in which circuit patterns are printed. Then, the resultant layers are stacked and fired in order to be integrated.

In a space between a lower surface of the second solid electrolyte layer 6 and an upper surface of the first solid electrolyte layer 4 on one end (left side in FIG. 1) of the sensor element 101, a gas introduction aperture 10, a first diffusion control section 11, a buffer space 12, a second diffusion control section 13, a first internal space 20, a third diffusion control section 30, and a second internal space 40 are formed in one adjacent to the next in this order so as to be communicated with one another.

The gas introduction aperture 10, the buffer space 12, the first internal space 20, and the second internal space 40 are each part of a space in the sensor element 101 formed by slotting the spacer layer 5. The upper, lower, and side portions of the slotted space are defined by the lower surface of the second solid electrolyte layer 6, the upper surface of the first solid electrolyte layer 4, and a side surfaces of the spacer layer 5, respectively.

The first diffusion control section 11, the second diffusion control section 13, and the third diffusion control section 30 are each formed of two slits, of which the lateral sides are longer (the longitudinal direction of openings extend in a direction perpendicular to the face of FIG. 1). A portion from the gas introduction aperture 10 to the second internal space 40 is also referred to as an object gas flow path.

A reference gas introduction space 43 is formed at a position further away from the one end side than the object gas flow path, and between an upper surface of the second substrate layer 2 and a lower surface of the first solid electrolyte layer 4. A side portion of the reference gas introduction space 43 is defined by a side surface of the third substrate layer 3. Into the reference gas introduction space 43, a reference gas used in measurement of the concentration of NOx, for example, atmosphere, is introduced.

A reference gas introduction layer 48 is formed of a porous alumina and exposed to the reference gas introduction space 43. The reference gas is introduced to the reference gas introduction layer 48 through the reference gas introduction space 43. The reference gas introduction layer 48 is formed so as to cover a reference electrode 42. The reference gas introduction layer 48 introduces the reference gas in the reference gas introduction space 43 to the reference electrode 42 while imparting a specified diffusion resistance to the reference gas. Since the reference gas introduction layer 48 is a porous body, the heat conductivity thereof is lower compared to the dense first solid electrolyte layer 4 or the third substrate layer 3. The reference gas introduction layer 48 is formed so as to be exposed to the reference gas introduction space 43 only on the other end side (right side in FIG. 1) of the sensor element 101 further away from the one end side than the reference electrode 42 is. For this reason, compared to a case in which the reference gas introduction space 43 is formed so as to extend to a position, for example, immediately below the reference electrode 42 in FIG. 1, the length of a path of the reference gas from the reference gas introduction space 43 to the reference electrode 42 is increased, and accordingly, a specified high diffusion resistance is easily imparted to the reference gas using the reference gas introduction layer 48. Here, as the diffusion resistance imparted to the reference gas increases, the amount of oxygen included in the reference gas that reaches the reference electrode 42 decreases. Thus, when measuring the concentration of oxygen (partial pressure of oxygen) in the object gas flow path using the reference electrode 42 as described later, by imparting a specified high diffusion resistance, detection of a small change in the concentration of oxygen in the object gas flow path is facilitated. This can improve the detection sensitivity. In addition, in the case in which the reference gas introduction space 43 is formed so as to extend to a position, for example, immediately below the reference electrode 42 in FIG. 1, poisoning of the reference electrode 42 by the reference gas easily occurs. The present embodiment can prevent the occurrence of this poisoning.

The reference electrode 42 is formed so as to be interposed between the upper surface of the third substrate layer 3 and the first solid electrolyte layer 4. As described above, the reference gas introduction layer 48, which is connected to the reference gas introduction space 43, is formed around the reference electrode 42. The reference electrode 42 is formed directly on the lower surface of the first solid electrolyte layer 4. The reference electrode 42 is covered with the reference gas introduction layer 48 except for a portion contacting the lower surface of the first solid electrolyte layer 4. As described later, the concentration of oxygen (partial pressure of oxygen) in the first internal space 20 and the second internal space 40 can be measured using the reference electrode 42.

In the object gas flow path, the gas introduction aperture 10 is open to an external space. The object gas is introduced from the external space into the sensor element 101 through the gas introduction aperture 10. The first diffusion control section 11 is a portion that imparts a specified diffusion resistance to the object gas introduced through the gas introduction aperture 10. The buffer space 12 is a space formed in order to guide the object gas introduced from the first diffusion control section 11 to the second diffusion control section 13. The second diffusion control section 13 is a portion that imparts a specified diffusion resistance to the object gas introduced from the buffer space 12 to the first internal space 20. When the object gas is introduced from the outside of the sensor element 101 into the first internal space 20, the object gas is rapidly introduced into the sensor element 101 from the gas introduction aperture 10 due to a change in the pressure of the object gas (when the object gas is an exhaust gas from an automobile, pulsing of an exhaust pressure) in the external space. The object gas is introduced into the first internal space 20 after variation in the concentration of the object gas is canceled out while passing through the first diffusion control section 11, the buffer space 12, and the second diffusion control section 13 instead of being directly introduced into the first internal space 20. By doing this, the variation in the concentration of the object gas introduced into the first internal space 20 is decreased to a level that can be almost negligible. The first internal space 20 is a space that regulates a partial pressure of oxygen in the object gas introduced through the second diffusion control section 13. This partial pressure of oxygen is regulated by an operation of a main pump cell 21.

The main pump cell 21 is an electrochemical pump cell that includes an inner pump electrode 22, an outer pump electrode 23, and the second solid electrolyte layer 6 interposed between the inner and outer pump electrodes 22 and 23. The inner pump electrode 22 has a top electrode unit 22a provided on substantially entirely on a portion of the lower surface of the second solid electrolyte layer 6 facing the first internal space 20. The outer pump electrode 23 is provided in an area corresponding to the top electrode unit 22a on the upper surface of the second solid electrolyte layer 6 so as to be exposed to the external space.

The inner pump electrode 22 is formed in an area surrounded by portions of the upper and lower solid electrolyte layers (the second solid electrolyte layer 6 and the first solid electrolyte layer 4) which define the first internal space 20, and portions of the spacer layer 5 serving as side walls. Specifically, the inner pump electrode 22 is formed of the top electrode unit 22a, a bottom electrode unit 22b, and side electrode units (not shown). The top electrode unit 22a is formed on the bottom surface of the second solid electrolyte layer 6, which serves as a top surface of the first internal space 20. The bottom electrode unit 22b is formed directly on the upper surface of the first solid electrolyte layer 4, which serves as a bottom surface of the first internal space 20. The side electrode units are formed on side wall surfaces (inner surfaces) of the spacer layer 5, which serve as side wall portions of the first internal space 20, so as to connect the top electrode unit 22a to the bottom electrode unit 22b, thereby forming a tunnel-like structure in a portion in which the side electrode units are disposed.

The inner pump electrode 22 and the outer pump electrode 23 are each formed as a porous cermet electrode (for example, a cermet electrode formed of Pt including 1% Au and $ZrO_2$). The inner pump electrode 22, which contacts the object gas, is formed of a material of which the capacity to reduce the NOx component in the object gas is decreased.

In the main pump cell 21, a desired pump voltage Vp0 is applied between the inner pump electrode 22 and the outer pump electrode 23 to cause a pump current Ip0 to flow in a positive or negative direction between the inner pump electrode 22 and outer pump electrode 23. Thus, oxygen in the first internal space 20 can be pumped out to the external space, or oxygen in the external space can be pumped into the first internal space 20.

In order to detect the concentration of oxygen (partial pressure of oxygen) in the atmosphere in the first internal space 20, an electrochemical sensor cell, that is, a main-pump-controlling oxygen partial pressure detection sensor cell 80 is formed of the inner pump electrode 22, the second solid electrolyte layer 6, the spacer layer 5, the first solid electrolyte layer 4, and the reference electrode 42.

By measuring an electromotive force V0 in the main-pump-controlling oxygen partial pressure detection sensor cell 80, the concentration of oxygen (partial pressure of oxygen) in the first internal space 20 can be recognized. In addition, the pump current Ip0 is controlled by feedback control performed on the pump voltage Vp0 of a variable power source 25 such that the electromotive force V0 is constant. Thus, the concentration of oxygen in the first internal space 20 can be maintained at a specified constant value.

The third diffusion control section 30 imparts a specified diffusion resistance to the object gas, of which the concentration of oxygen (partial pressure of oxygen) is controlled by an operation of the main pump cell 21 in the first internal space 20, and introduces the object gas into the second internal space 40.

The second internal space 40 is a space that performs a process for measuring the concentration of nitrogen oxide (NOx) in the object gas having been introduced through the third diffusion control section 30. The concentration of NOx is mainly measured in the second internal space 40, in which the concentration of oxygen is regulated using an auxiliary pump cell 50, by an operation of a measurement pump cell 41.

After the concentration of oxygen (partial pressure of oxygen) has been initially regulated in the first internal space 20, in the second internal space 40, the partial pressure of oxygen in the object gas having been introduced through the third diffusion control section 30 is further regulated using the auxiliary pump cell 50. Thus, the concentration of oxygen in the second internal space 40 can be highly accurately maintained at a constant level, thereby allowing the gas sensor 100 to accurately measure the concentration of NOx.

The auxiliary pump cell 50 is an auxiliary electrochemical pump cell that includes an auxiliary pump electrode 51, the outer pump electrode 23 (this electrode is not limited to the outer pump electrode 23, and an adequate electrode outside the sensor element 101 is sufficient), and the second solid electrolyte layer 6. The auxiliary pump electrode 51 has a top electrode unit 51a provided substantially entirely on a portion of the lower surface of the second solid electrolyte layer 6 facing the second internal space 40.

The auxiliary pump electrode 51 is arranged in the second internal space 40 so as to have a tunnel-like structure similar to that of the above-described inner pump electrode 22 provided in the first internal space 20. Specifically, the tunnel-like structure is formed of the top electrode unit 51a, a bottom electrode unit 51b, and side electrode units (not shown). The top electrode unit 51a is formed on the second solid electrolyte layer 6, which serves as a top surface of the second internal space 40. The bottom electrode unit 51b is formed directly on the upper surface of the first solid electrolyte layer 4, which serves as a bottom surface of the second internal space 40. The side electrode units, which connect the top electrode unit 51a to the bottom electrode unit 51b, are formed on the side wall surfaces of the spacer layer 5 serving as side walls of the second internal space 40. As is the case with the inner pump electrode 22, the auxiliary pump electrode 51 is also formed of a material of which the capacity to reduce the NOx component in the object gas is decreased.

In the auxiliary pump cell 50, by applying a desired voltage Vp1 between the auxiliary pump electrode 51 and the outer pump electrode 23, oxygen in an atmosphere in the second internal space 40 can be pumped out to the external space, or oxygen in the external space can be pumped into the second internal space 40.

In order to control the partial pressure of oxygen in the atmosphere in the second internal space 40, an electrochemical sensor cell, that is, an auxiliary-pump-controlling oxygen partial pressure detection sensor cell 81 is formed of the auxiliary pump electrode 51, the reference electrode 42, the second solid electrolyte layer 6, the spacer layer 5, and the first solid electrolyte layer 4.

Using a variable power source 52, the voltage of which is controlled in accordance with an electromotive force V1 detected by the auxiliary-pump-controlling oxygen partial pressure detection sensor cell 81, the auxiliary pump cell 50 performs pumping. Thus, the partial pressure of oxygen in the atmosphere in the second internal space 40 is controlled to a partial pressure that is sufficiently lower so as not to substantially affect measurement of NOx.

In addition, a pump current Ip1 here is used to control the electromotive force of the main-pump-controlling oxygen partial pressure detection sensor cell 80. Specifically, the pump current Ip1 is input as a control signal to the main-pump-controlling oxygen partial pressure detection sensor cell 80, and the electromotive force V0 thereof is controlled. Thus, the gradient of the partial pressure of oxygen in the object gas, which is introduced into the second internal space 40 through the third diffusion control section 30, is controlled such that the gradient of the partial pressure of oxygen is always constant. When the gas sensor 100 is used as a NOx sensor, by operations of the main pump cell 21 and the auxiliary pump cell 50, the concentration of oxygen in the second internal space 40 is maintained at a constant value of about 0.001 ppm.

The measurement pump cell 41 measures the concentration of NOx in the object gas in the second internal space 40. The measurement pump cell 41 is an electrochemical pump cell formed of a measurement electrode 44, the outer pump electrode 23, the second solid electrolyte layer 6, the spacer layer 5, and the first solid electrolyte layer 4. The measurement electrode 44 is directly provided at a position on a portion of the upper surface of the first solid electrolyte layer 4 that faces the second internal space 40, separated away from the third diffusion control section 30. The measurement electrode 44 is provided at a position opposite the reference electrode 42 with the first solid electrolyte layer 4 interposed therebetween.

The measurement electrode 44 is a porous cermet electrode. The measurement electrode 44 also functions as a NOx reduction catalyst to reduce NOx included in the atmosphere in the second internal space 40. The measurement electrode 44 is covered with a fourth diffusion control section 45.

The fourth diffusion control section 45 is a film formed of a porous body, a main component of which is alumina ($Al_2O_3$). The fourth diffusion control section 45 limits the amount of NOx flowing to the measurement electrode 44 and serves as a protective film for the measurement electrode 44. In the measurement pump cell 41, oxygen produced due to decomposition of nitrogen oxide in the atmosphere around the measurement electrode 44 can be pumped out, and the amount of the produced oxygen can be detected as a pump current Ip2.

In order to detect the partial pressure of oxygen around the measurement electrode 44, an electrochemical sensor cell, that is, a measurement-pump-controlling oxygen partial pressure detection sensor cell 82 is formed of the first solid electrolyte layer 4, the measurement electrode 44, and the reference electrode 42. A variable power source 46 is controlled in accordance with an electromotive force V2, which is detected by the measurement-pump-controlling oxygen partial pressure detection sensor cell 82.

The object gas having been introduced into the second internal space 40 reaches the measurement electrode 44 through the fourth diffusion control section 45 while the partial pressure of oxygen is being controlled. Oxygen is produced due to reduction of nitrogen oxide ($2NO \rightarrow N_2+O_2$) in the object gas around the measurement electrode 44. The produced oxygen is subject to pumping using the measurement pump cell 41. In so doing, a voltage Vp2 of the variable power source 46 is controlled so that a control voltage V2 detected by the measurement-pump-controlling oxygen partial pressure detection sensor cell 82 is constant. Since the amount of oxygen produced around the measurement electrode 44 is proportional to the concentration of nitrogen oxide in the object gas, the concentration of nitrogen oxide in the object gas is calculated from the pump current Ip2 in the measurement pump cell 41.

An electrochemical sensor cell 83 is formed of the second solid electrolyte layer 6, the spacer layer 5, the first solid electrolyte layer 4, the outer pump electrode 23, and the reference electrode 42. The partial pressure of oxygen in the object gas outside the sensor can be detected by an electromotive force Vref obtained by the sensor cell 83.

In the gas sensor 100 having the above-described structure, by operating the main pump cell 21 and the auxiliary pump cell 50, an object gas, of which the partial pressure of oxygen is always maintained at a constant small value (a value that does not substantially affect measurement of NOx), is introduced to the measurement pump cell 41. Thus, the concentration of NOx in the object gas can be recognized in accordance with the pump current Ip2 that flows due to pumping of oxygen, which is produced by reducing NOx substantially in proportion to the concentration of NOx in the object gas, out of the measurement pump cell 41.

In addition, in order to increase the oxygen ion conductivity of the solid electrolyte, the sensor element 101 includes a heater unit 70. The heater unit 70 heats and keeps warm the sensor element 101 to adjust the temperature. The heater unit 70 includes heater electrodes 71, a heater 72, a through hole 73, a heater insulation layer 74, and leads 76.

The heater electrodes 71 are formed so as to contact a lower surface of the first substrate layer 1. By connecting the heater electrodes 71 to an external power source, the external power can be supplied to the heater unit 70.

The heater 72 is an electrical resistor formed so as to be interposed between the second substrate layer 2 and the third substrate layer 3 from below and above. The heater 72 is connected to the heater electrodes 71 through the leads 76 and the through hole 73, generates heat when the external power is supplied thereto through the heater electrodes 71, and heats and keeps warm the solid electrolyte that forms the sensor element 101.

The heater 72 is embedded in an entire area corresponding to the first internal space 20 to the second internal space 40. By doing this, heater 72 can adjust the temperature of the entire sensor element 101 so as to cause the above-described solid electrolyte to be activated.

The heater insulation layer 74 is formed on upper and lower surfaces of the heater 72 using porous alumina, which is made of an insulator such as alumina. The heater insulation layer 74 is formed in order to electrically insulate the second substrate layer 2 from the heater 72 and electrically insulate the third substrate layer 3 from the heater 72. As illustrated in FIG. 1, part of the heater insulation layer 74 is exposed to the reference gas introduction space 43.

Figure 2:
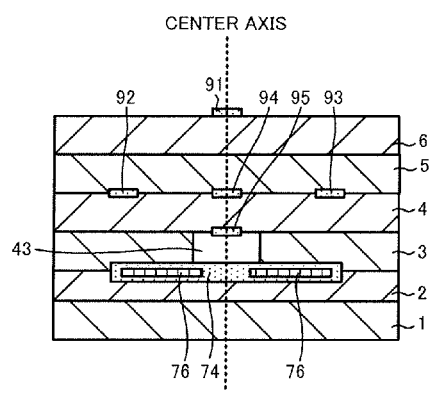
FIG. 2 is a sectional view of the gas sensor 100 illustrated in FIG. 1 taken along line A-A in FIG. 1.

Although illustration is omitted from FIG. 1, the measurement electrode 44, the reference electrode 42, the inner pump electrode 22, the outer pump electrode 23, and the auxiliary pump electrode 51 are each electrically connected to a corresponding one of plurality of leads in a one-to-one relationship. The leads are formed so as to extend toward the other side (right side in FIG. 1) of the sensor element 101. Voltage or current can be applied to each electrode, and voltage or current at each electrode can be measured through these leads. Arrangement of these leads in the sensor element 101 is illustrated in FIG. 2. FIG. 2 is a sectional view of the gas sensor 100 taken along line A-A in FIG. 1.

Referring to FIG. 2, a lead 91 is electrically connected to the outer pump electrode 23, a lead 92 is electrically connected to the bottom electrode unit 22b of the inner pump electrode 22, a lead 93 is electrically connected to the bottom electrode unit 51b of the auxiliary pump electrode 51, a lead 94 is electrically connected to the measurement electrode 44, and lead 95 is electrically connected to the reference electrode 42. As can be seen from FIG. 2, when a direction perpendicular to a direction in which a multilayer body is stacked is a lateral direction, the leads 91 to 95 are laterally symmetrically arranged. In other words, the leads 91 to 95 are axially symmetrically arranged with respect to the center axis of the lateral direction illustrated in FIG. 2. In the present embodiment, as illustrated in FIG. 2, the heater insulation layer 74 and the leads 76 of the heater unit 70 are also laterally symmetrically arranged similarly to the leads 91 to 95.

Next, an example of a production method of the sensor element 101 of the above-described gas sensor 100 will be described below. Initially, six ceramic green sheets, which have not been fired, are prepared. The ceramic green sheets include an oxygen ion conductive solid electrolyte such as zirconia as a ceramic component. Sheet holes used for positioning performed for printing or stacking, necessary through holes, and the like are formed in the green sheets in advance. A space for the object gas flow path is formed in advance in the green sheet used for the spacer layer 5 by punching or the like. Likewise, a space for the reference gas introduction space 43 is formed in the green sheet used for the third substrate layer 3. The six ceramic green sheets undergo pattern printing to form variety of patterns and drying processes, corresponding to the first substrate layer 1, the second substrate layer 2, the third substrate layer 3, the first solid electrolyte layer 4, the spacer layer 5, and the second solid electrolyte layer 6 respectively. Specifically, the patterns to be formed include, for example, patterns of the above-described components such as the electrodes, leads, the fourth diffusion control section 45, the reference gas introduction layer 48, and the heater unit 70. In order to print patterns, pastes for forming a pattern are prepared corresponding to characteristics required for respective forming objects. The pastes are applied onto the green sheets using known screen printing method. The drying process is also performed using known drying means. When pattern printing and drying processes are complete, a printing and drying process for adhesive paste is performed in order to stack and bond the green sheets corresponding to the layers to one another. The green sheets on which the adhesive paste is applied are stacked one on top of one another in a specified order while the green sheets are positioned using the sheet holes. The resultant structure is pressure-bonded under specified temperature and pressure conditions in order to form a single multilayer body. The multilayer body obtained as described above includes a plurality of sensor element 101. The multilayer body is cut into pieces, each of which has the size of the sensor element 101. The cut pieces of the multilayer body are fired at a specified firing temperature to obtain the sensor elements 101. Thus, the obtained sensor elements 101 are each housed into a specified housing to be mounted in a main body (not shown) of the gas sensor 100, thereby obtaining the gas sensor 100.

Relationships between elements of the present embodiment and elements of the present invention will be clarified below. The first substrate layer 1, the second substrate layer 2, the third substrate layer 3, the first solid electrolyte layer 4, the spacer layer 5, and the second solid electrolyte layer 6 of the present embodiment correspond to a multilayer body of the present invention. The measurement electrode 44 and the reference electrode 42 respectively correspond to a measurement electrode and a reference electrode. The measurement-pump-controlling oxygen partial pressure detection sensor cell 82 and the measurement pump cell 41 correspond to detection unit. The heater 72 corresponds to a heater. The inner pump electrode 22 corresponds to an inner main pump electrode. The outer pump electrode 23 corresponds to an outer main pump electrode. The main pump cell 21 corresponds to a main pump cell. The auxiliary pump electrode 51 corresponds to an inner auxiliary pump electrode. The outer pump electrode 23 corresponds to an outer auxiliary pump electrode. The auxiliary pump cell 50 corresponds to an auxiliary pump cell. The leads 92 to 95 correspond to leads. The heater insulation layer 74 corresponds to a heater insulation layer.

In the gas sensor 100 according to the present embodiment described above in detail, the reference electrode 42 is formed directly on the surface of the first solid electrolyte layer 4, on which the measurement electrode 44 is formed, on the side opposite the side on which the measurement electrode 44 is formed. That is, the reference electrode 42 and the measurement electrode 44 are formed directly on the same first solid electrolyte layer 4. Thus, heat from the heater 72 is transferred from the third substrate layer 3 and the first solid electrolyte layer 4 in this order. The heat is transferred from the heater 72 to the reference electrode 42 and the measurement electrode 44 through the same first solid electrolyte layer 4. Since the reference electrode 42 is covered with the reference gas introduction layer 48 formed of a porous body, compared to transference of heat from the heater 72 to the reference electrode 42 through the first solid electrolyte layer 4 on which the reference electrode 42 is formed directly, transference of heat from the heater 72 to the reference electrode 42 through the reference gas introduction layer 48 is smaller. Thus, compared to a gas sensor, for example, such as a gas sensor 300 illustrated in FIG. 6, in which a reference electrode and a measurement electrode are formed on different solid electrolyte layers and not only the solid electrolyte layer but also a reference gas introduction layer are present between the reference electrode and the measurement electrode, occurrence of a situation that causes the temperature difference between the reference electrode 42 and the measurement electrode 44 due to heat from the heater 72 is suppressed. Thus, variation in the electromotive force V2 generated between the reference electrode 42 and the measurement electrode 44 can be decreased.

Since the inner pump electrode 22 is also formed directly on the first solid electrolyte layer 4 on which the measurement electrode 44 is formed, occurrence of a situation that causes the temperature difference between the reference electrode 42 and the inner pump electrode 22 is suppressed. Thus, variation in the electromotive force V0 generated between the reference electrode 42 and the inner pump electrode 22 can be decreased.

Since the auxiliary pump electrode 51 is also formed directly on the first solid electrolyte layer 4 on which the measurement electrode 44 is formed, occurrence of a situation that causes the temperature difference between the reference electrode 42 and the auxiliary pump electrode 51 is suppressed. Thus, variation in the electromotive force V1 generated between the reference electrode 42 and the auxiliary pump electrode 51 can be decreased.

In addition, the leads 92 to 95 are, when a direction perpendicular to a direction in which the layers of the sensor element 101 are stacked is the lateral direction (lateral direction in FIG. 2), laterally symmetrically arranged in a section.

This section is perpendicular to a direction extending from the one end to the other end of the sensor element 101 on the other end side (right side in FIG. 1) further away from the one end side than the measurement electrode 44, the reference electrode 42, the inner pump electrode 22, and the auxiliary pump electrode 51 are. Thus, compared to a case in which the leads are laterally asymmetrically arranged, warpage of the sensor element 101 in the lateral direction, which is caused by a difference in the thermal expansion coefficient between the leads 92 to 95 and the solid electrolyte layers included in the sensor element 101, is decreased. That is, in the production of the sensor element, when firing the multilayer body formed of the stacked green sheets on which patterns of the electrodes, the leads, the insulation layer, the resistance heater element, and the like are screen-printed, the sensor element 101 may warp in the lateral direction in FIG. 2 due to the difference in the thermal expansion coefficient between the solid electrolyte layers and the leads 92 to 95. The amount of this warpage can be decreased.

The heater 72 is formed at a position away from the reference electrode 42 with the third substrate layer 3 interposed therebetween. The third substrate layer 3 is a solid electrolyte layer contacting the surface of the first solid electrolyte layer 4 on which the reference electrode 42 is formed directly on the reference electrode 42 side (lower surface). Thus, compared to a case in which two or more solid electrolyte layers are present between the reference electrode 42 and the heater 72, the distance between the heater 72 and the reference electrode 42 and the distance between the heater 72 and the measurement electrode 44 are decreased, thereby suppressing occurrence of a situation that causes the temperature difference between the reference electrode 42 and the measurement electrode 44.

The third substrate layer 3 is a solid electrolyte layer contacting the surface of the first solid electrolyte layer 4 on which the reference electrode 42 is formed directly on the reference electrode 42 side (lower surface). The reference gas introduction space 43 is a hole formed in the third substrate layer 3. The heater insulation layer 74 is exposed to the reference gas introduction space 43. Thus, the reference gas introduction space 43 also functions as a pressure releasing hole, thereby eliminating the necessity of forming a separate pressure releasing hole. That is, the internal pressure of the heater insulation layer 74 formed of a porous body may increase because of expansion of a gas in holes of the porous body due to heat from the heater 72. When the heater insulation layer 74 is exposed to the reference gas introduction space 43, the increase in the internal pressure can be suppressed by releasing the gas in the porous body to the reference gas introduction space 43.

The present invention is not limited to the above-described embodiment. It is clear that the present invention can be implemented in a variety of modes within the technical scope of the present invention.

Figure 3:
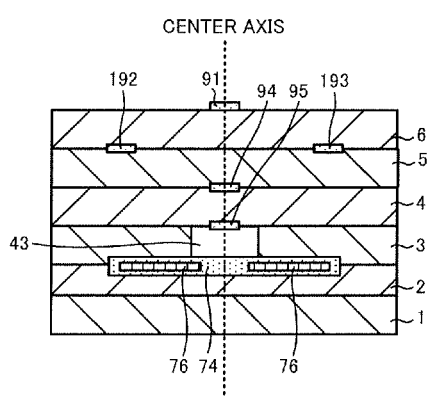
FIG. 3 is a sectional view of the arrangement of leads in a modified example.

For example, in the above-described embodiment, the leads 91 to 95, the leads 76, and the heater insulation layer 74 are arranged as illustrated in FIG. 2. However, it is sufficient that the leads 92 to 95 are, when a direction perpendicular to a direction in which the layers of the sensor element 101 are stacked is the lateral direction (lateral direction in FIG. 2), laterally symmetrically arranged in the section. This section is perpendicular to a direction extending from the one end to the other end of the sensor element 101 on the other end side (right side in FIG. 1) further away from the one end side than the measurement electrode 44, the reference electrode 42, the inner pump electrode 22, and the auxiliary pump electrode 51 are. For example, an arrangement as illustrated in FIG. 3 is also sufficient. In FIG. 3, components the same as those in FIG. 2 are denoted by the same reference numerals as those in FIG. 2, and the description thereof is omitted. A lead 192 is electrically connected to the top electrode unit 22a of the inner pump electrode 22, and a lead 193 is electrically connected to the top electrode unit 51a of the auxiliary pump electrode 51. The lead 91, the leads 76, and the heater insulation layer 74 are not necessarily laterally symmetrically arranged. Also in this case, because of the laterally symmetrical arrangement of the leads 92 to 95, effects of decreasing lateral warpage of the sensor element 101 can be produced.

In the above-described embodiment, the auxiliary pump cell 50 is formed of the auxiliary pump electrode 51, the outer pump electrode 23 and the second solid electrolyte layer 6. However, instead of the outer pump electrode 23, another electrode provided outside the sensor element 101 (referred to as an outer auxiliary pump electrode hereafter) may be used. In this case, a lead electrically connected to this outer auxiliary pump electrode may be formed in addition to the leads 91 to 95. Also in this case, as long as the leads 92 to 95 are laterally symmetrically arranged, the effects of decreasing lateral warpage of the sensor element 101 can be produced. Alternatively, the leads 91 to 95 and the lead electrically connected to the outer auxiliary pump electrode may be, when a direction perpendicular to a direction in which the layers of the sensor element 101 are stacked is the lateral direction, laterally symmetrically arranged in a section. This section is perpendicular to a direction extending from the one end to the other end of the sensor element 101 on the other end side (right side in FIG. 1) further away from the one end side than the measurement electrode 44, the reference electrode 42, the inner pump electrode 22, the outer pump electrode 23, the auxiliary pump electrode 51 and the outer auxiliary pump electrode are.

In the above-described embodiment, the reference electrode 42 is provided at a position opposite the measurement electrode 44 (immediately below the measurement electrode 44) with the first solid electrolyte layer 4 therebetween. The positions of the reference electrode 42 and the measurement electrode 44 are not limited to these. The reference electrode 42 and the measurement electrode 44 may be provided at positions shifted from the positions opposite to each other. Also in this case, the above-described effects of suppressing occurrence of a situation that causes the temperature difference between the reference electrode 42 and the measurement electrode 44 can be obtained.

In the above-described embodiment, the inner pump electrode 22 has a tunnel-like structure formed of the top electrode unit 22a, the bottom electrode unit 22b, and the side electrode units. However, the structure of the inner pump electrode 22 is not limited to the tunnel-like structure. For example, the inner pump electrode 22 may be only formed of the top electrode unit 22a or the bottom electrode unit 22b, or the like. When the inner pump electrode 22 has the bottom electrode unit 22b formed directly on the first solid electrolyte layer 4, on which the measurement electrode 44 and the reference electrode 42 are formed, variation in the electromotive force V2 generated between the inner pump electrode 22 and the reference electrode 42 can be decreased. Thus, it is preferable that the inner pump electrode 22 have such a bottom electrode unit 22b. Likewise, the structure of the auxiliary pump electrode 51 is not limited to the tunnel-like structure. It is preferable that the auxiliary pump electrode 51 have the bottom electrode unit 51b because variation in the electromotive force V1 generated between the reference electrode 42 and the auxiliary pump electrode 51 can be decreased.

In the above-described embodiment, pumping is performed using the measurement pump cell 41 with the voltage Vp2 of the variable power source 46 controlled such that the control voltage V2 detected by the measurement-pump-controlling oxygen partial pressure detection sensor cell 82 is constant. The pump current Ip2 flowing at this time is used to calculate the concentration of nitrogen oxide in the object gas. However, the concentration of nitrogen oxide in the object gas may be calculated using another method. For example, when an oxygen partial pressure detection unit as an electrochemical sensor cell is formed by combining the measurement electrode 44, the first solid electrolyte layer 4, and the reference electrode 42, an electromotive force, which corresponds to the difference between the amount of oxygen produced due to reduction of NOx in the atmosphere around the measurement electrode 44 and the amount of oxygen included in the reference atmosphere, can be detected. By doing this, the concentration of the NOx component in the object gas can also be obtained. In this case, the electrochemical sensor cell formed of the measurement electrode 44, the first solid electrolyte layer 4, and the reference electrode 42 corresponds to a detection unit of the present invention.

EXAMPLES

First Example and First Comparative Example

Figure 4:
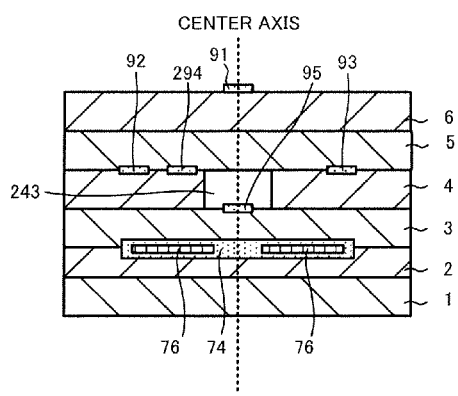
FIG. 4 is an explanatory view of the arrangement of leads in a sensor element of a first comparative example.
Figure 6:
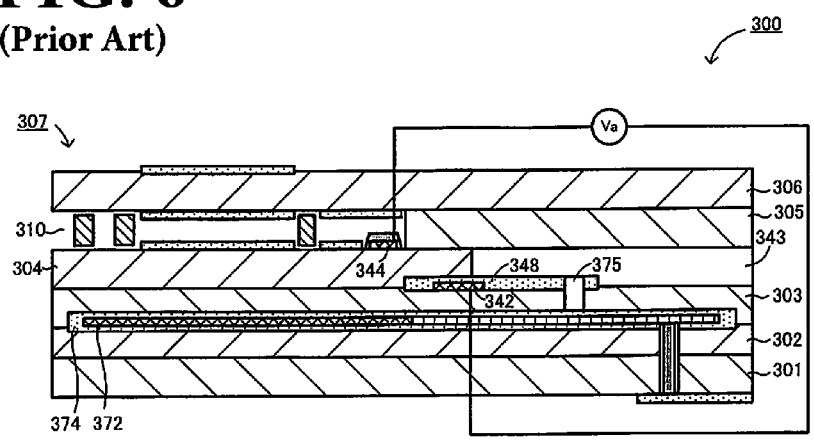
FIG. 6 is a schematic sectional view of a related-art gas sensor 300.

As a first example, 15 sensor elements 101 illustrated in FIGS. 1 and 2 are produced using the above-described production method. As a first comparative example, 15 sensor elements each similar to a sensor element 307 illustrated in FIG. 6 are produced. That is, each of these sensor elements has the structure similar to that of the first example except that a reference electrode and a measurement electrode are formed on different solid electrolyte layers, not only the solid electrolyte layer but also a reference gas introduction space are disposed between the reference electrode and the measurement electrode, the reference gas introduction space is formed in a first solid electrolyte layer, and a pressure releasing hole and the reference gas introduction space are separately formed. In the first comparative example, leads are arranged differently from those in the first example. FIG. 4 illustrates the arrangement of the leads of the first comparative example. In FIG. 4, components the same as those in FIG. 2 are denoted by the same reference numerals as those in FIG. 2, and the description thereof is omitted. In the first comparative example, a reference gas introduction space 243 is formed at a position between the upper surface of the third substrate layer 3 and the lower surface of the spacer layer 5 while the side portion thereof is defined by the side surface of the first solid electrolyte layer 4. Similar to the lead 94, a lead 294 of the first comparative example is electrically connected to the measurement electrode. However, different from that of the first example, the lead 294 is arranged at a position shifted from the center axis in FIG. 4. Thus, different from the leads 92 to 95 of the first example, the leads 92, 93, 294, and 95 are laterally asymmetrically arranged.

First Evaluation Test

The sensor elements of the first example and the first comparative example were maintained at a normal operating temperature (800° C.) in the atmosphere using the heater. An electromotive force between the reference electrode and the measurement electrode was measured. The measurement was performed on five sensor elements of each of the first example and the first comparative example. The range of variation (difference between the maximum and the minimum electromotive forces) of each of five measured electromotive forces was calculated. The results were 7 mV for the sensor elements of the first example, and 14 mV for the sensor elements of the first comparative example.

As a result, it was found that, for the sensor elements of the first example, variation in the electromotive force was decreased because a situation that caused the temperature difference between the reference electrode 42 and the measurement electrode 44 due to heat from the heater 72 was suppressed. This was achieved since the reference electrode 42 and the measurement electrode 44 were formed on a single solid electrolyte layer, and the reference electrode 42 was covered with the reference gas introduction layer 48 except for a surface that contacted the solid electrolyte layer, on which the reference electrode 42 was formed directly.

Second Evaluation Test

Figure 5:
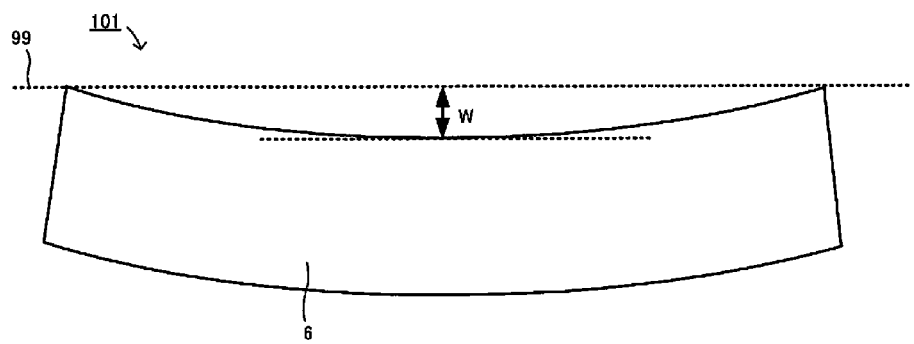
FIG. 5 is an explanatory view illustrating the amount of warpage W of a sensor element.

The amounts of warpage in the lateral direction of the sensor elements of the first example and the first comparative example were measured as follows. That is, as illustrated in FIG. 5, the maximum distance between each sensor element and a line 99 connecting the one end to the other end of the sensor element was measured as the warpage amount W. FIG. 5 is a top view of the sensor element 101 seen from the second solid electrolyte layer 6 side. The vertical direction in FIG. 5 is the lateral direction in FIG. 2. In FIG. 5, illustration of the outer pump electrode 23 and the lead 91 are omitted. The warpage amounts W were measured for 15 sensor elements of the first example and 15 sensor elements of the first comparative example, and the averages of the measured values were calculated. The results were 65 μm for the first example, and 180 μm for the first comparative example.

As a result, it was found that the warpage amount W of the sensor element 101 of the first example was smaller due to the laterally symmetrical arrangement of the leads 92 to 95.

The present application claims priority from Japanese Patent Application No. 2011-078373 filed on Mar. 31, 2011, the entire contents of which are incorporated herein by reference.

What is claimed is:

1. A gas sensor, comprising:
a multilayer body formed of a plurality of oxygen ion conductive dense solid electrolyte layers stacked one on top of one another, the multilayer body having therein an object gas flow path through which an object gas is introduced from one end of the multilayer body, and a reference gas introduction space through which a reference gas is introduced from the other end of the multilayer body, a concentration of a specified gas in the object gas being detected with reference to the reference gas;
a measurement electrode formed directly on one of the solid electrolyte layers facing the object gas flow path;
a reference electrode formed directly on a surface of the one solid electrolyte layer on which the measurement electrode is formed, the surface being a surface on a side opposite a side on which the measurement electrode is formed;
a reference gas introduction layer that covers the reference electrode, the reference gas introduction layer being formed of a porous body and formed so as to be exposed to the reference gas introduction space only on the other end side of the multilayer body at a position further away from the one end than the reference electrode is, the reference gas being introduced through the reference gas introduction layer from the reference gas introduction space to the reference electrode;
a detection unit that detects the concentration of the specified gas in the object gas in accordance with a first electromotive force generated between the reference electrode and the measurement electrode; and an another solid electrolyte layer having a first side opposite a second side, wherein the first side is located directly on the reference electrode side of the one solid electrolyte layer covering the reference electrode and in direct contact with a portion of the reference gas introduction layer and a heater is located on the second side.

2. The gas sensor according to claim 1, further comprising:
a main pump cell that applies a control voltage between an outer main pump electrode and an inner main pump electrode in accordance with a second electromotive force to pump oxygen into or out of the object gas flow path using the inner main pump electrode and the outer main pump electrode such that a concentration of oxygen in the object gas flow path reaches a specified main pump target concentration, the inner main pump electrode being formed on a solid electrolyte facing the object gas flow path, the outer main pump electrode being disposed on an outer surface of the multilayer body, the second electromotive force being generated between the inner main pump electrode and the reference electrode,
wherein the solid electrolyte layer on which the inner main pump electrode is formed directly is the one solid electrolyte layer on which the measurement electrode is formed.

3. The gas sensor according to claim 2, further comprising:
an auxiliary pump cell that applies another control voltage between an outer auxiliary pump electrode and an inner auxiliary pump electrode in accordance with a third electromotive force to pump oxygen into or out of the object gas flow path using the inner auxiliary pump electrode and the outer auxiliary pump electrode such that the concentration of oxygen in the object gas flow path reaches a specified auxiliary pump target concentration, the inner auxiliary pump electrode being formed on one of the solid electrolyte layers facing the object gas flow path, the outer auxiliary pump electrode being disposed on the outer surface of the multilayer body, the third electromotive force being generated between the inner auxiliary pump electrode and the reference electrode.

4. The gas sensor according to claim 3,
wherein the solid electrolyte layer on which the inner auxiliary pump electrode is formed directly is the one solid electrolyte layer on which the measurement electrode is formed.

5. The gas sensor according to claim 3, further comprising:
a plurality of leads each electrically connected to a corresponding one of the measurement electrode, the reference electrode, the inner main pump electrode, and the inner auxiliary pump electrode in a one-to-one relationship, the plurality of leads being formed so as to extend toward the other side of the multilayer body,
wherein the reference gas introduction space is a hole formed in the another solid electrolyte layer of the plurality of solid electrolyte layers,
wherein the plurality of leads are laterally symmetrically arranged in a section, the section being perpendicular to a direction extending from the one end to the other end of the multilayer body.

6. The gas sensor according to claim 1, further comprising:
a heater insulation layer formed of a porous body surrounding the heater,
wherein the reference gas introduction space is a hole formed in the another solid electrolyte layer of the plurality of solid electrolyte layers, and
part of the heater insulation layer is exposed to the reference gas introduction space.

* * * * *